(12) United States Patent
Fittipaldi et al.

(10) Patent No.: US 12,364,576 B2
(45) Date of Patent: Jul. 22, 2025

(54) SPLINT DEVICE FOR GUIDED SURGICAL ROBOT

(71) Applicant: NEOCIS INC., Miami, FL (US)

(72) Inventors: Mauro Fittipaldi, Miami, FL (US); Juan Salcedo, Coral Gables, FL (US); Melissa Francesca Gianello, Pembroke Pines, FL (US); Dennis Moses, Hollywood, FL (US)

(73) Assignee: NEOCIS INC., Miami, FL (US)

( * ) Notice: Subject to any disclaimer, the term of this patent is extended or adjusted under 35 U.S.C. 154(b) by 378 days.

(21) Appl. No.: 17/915,861

(22) PCT Filed: Mar. 30, 2021

(86) PCT No.: PCT/IB2021/052646
§ 371 (c)(1),
(2) Date: Sep. 29, 2022

(87) PCT Pub. No.: WO2021/198919
PCT Pub. Date: Oct. 7, 2021

(65) Prior Publication Data
US 2023/0149123 A1    May 18, 2023

Related U.S. Application Data

(60) Provisional application No. 63/001,998, filed on Mar. 30, 2020.

(51) Int. Cl.
*A61C 5/00* (2017.01)
*A61B 34/20* (2016.01)
(Continued)

(52) U.S. Cl.
CPC .............. *A61C 5/007* (2013.01); *A61B 34/20* (2016.02); *A61B 34/30* (2016.02); *A61B 2034/2046* (2016.02); *A61B 2090/363* (2016.02)

(58) Field of Classification Search
CPC . A61C 5/007; A61B 34/20; A61B 2034/2046; A61B 34/30; A61B 2090/363
See application file for complete search history.

(56) References Cited

U.S. PATENT DOCUMENTS 6,269,148 B1    7/2001  Jessop et al.
6,428,315 B1 *  8/2002  Prestipino ............ A61C 9/0006
                                                 433/45

(Continued)

FOREIGN PATENT DOCUMENTS

CN    105662618 A    6/2016
CN    108553186 A    9/2018
(Continued)

*Primary Examiner* — Ralph A Lewis
(74) *Attorney, Agent, or Firm* — Womble Bond Dickinson (US) LLP

(57) ABSTRACT

A splint device for robotically-guided surgery includes elongate co-extending first and second splint portions each defining spaced-apart relief holes between first and second ends. A first separability provision is disposed between and extends along the first and second splint portions. A tracking portion is engaged with and extends outwardly from the first or second splint portion and extending outwardly therefrom, and has a kinematic mount engaged therewith. A second separability provision extending between one of the relief holes of the first splint portion and one of the relief holes of the second splint portion, wherein the second separability provision is arranged to be severable so as to facilitate adjustability of a length of the first and second splint portions and the first separability provision. The splint device can include a tool calibration provision or a fiducial marker element disposed in a predetermined disposition relative to the kinematic mount.

25 Claims, 6 Drawing Sheets

Figure 1:
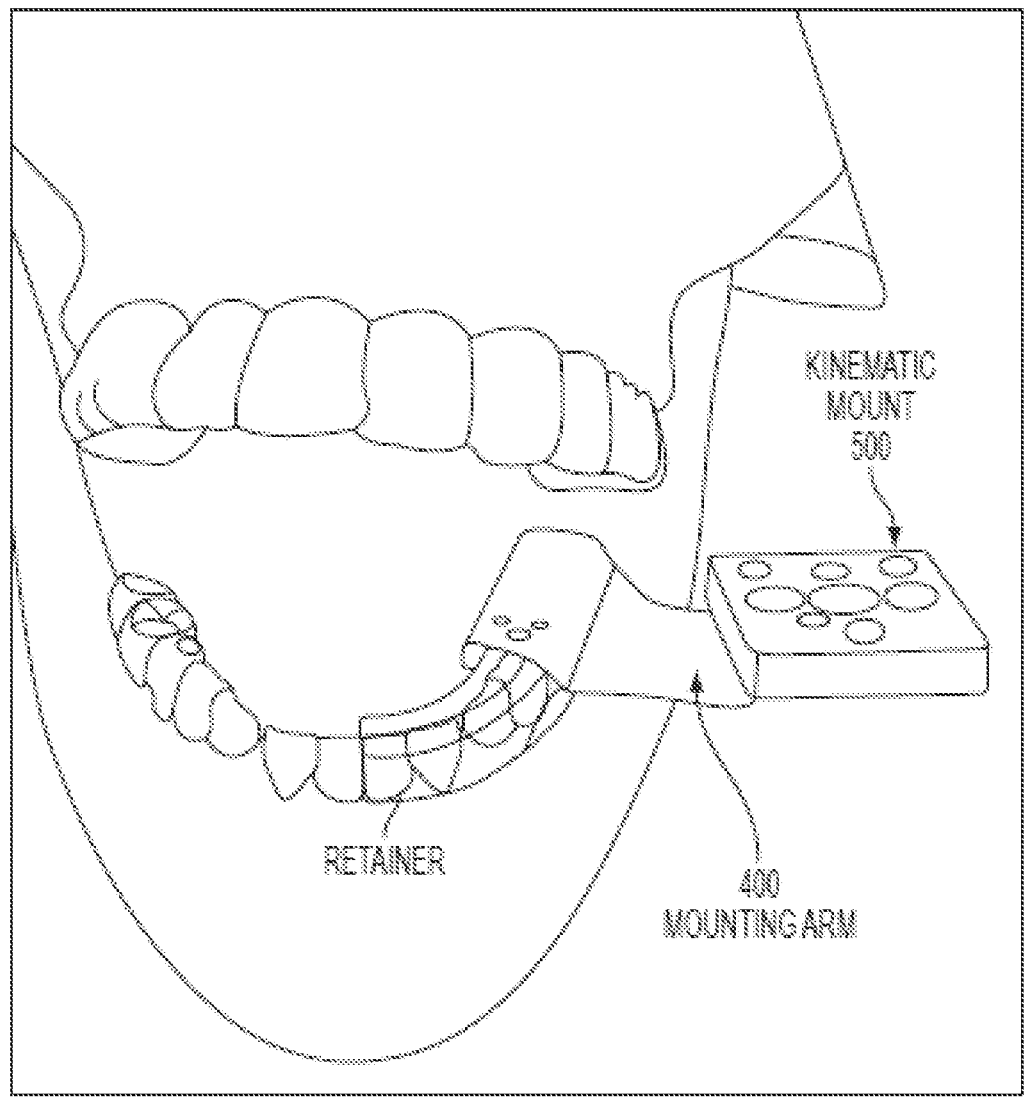

(51) Int. Cl.
*A61B 34/30* (2016.01)
*A61B 90/00* (2016.01)

(56) References Cited

U.S. PATENT DOCUMENTS

| | | | |
|---|---|---|---|
| 10,016,242 B2* | 7/2018 | Salcedo | A61B 34/20 |
| 10,639,128 B2* | 5/2020 | Grande | A61C 1/082 |
| 2005/0106529 A1* | 5/2005 | Abolfathi | A61C 9/0006 |
| | | | 433/41 |
| 2005/0228256 A1 | 10/2005 | Labadie et al. | |
| 2006/0281991 A1 | 12/2006 | Fitzpatrick et al. | |
| 2007/0202457 A1 | 8/2007 | Ho et al. | |
| 2009/0209852 A1 | 8/2009 | Mate et al. | |
| 2013/0009657 A1 | 1/2013 | Su et al. | |
| 2014/0272773 A1* | 9/2014 | Merritt | A61B 6/512 |
| | | | 433/29 |
| 2015/0133956 A1 | 5/2015 | Dayan et al. | |
| 2015/0147714 A1 | 5/2015 | Daon | |
| 2016/0278875 A1 | 9/2016 | Crawford et al. | |
| 2016/0310233 A1* | 10/2016 | Grande | A61C 1/084 |
| 2016/0367343 A1 | 12/2016 | Mozes et al. | |
| 2017/0105802 A1 | 4/2017 | Taraschi et al. | |
| 2017/0265974 A1 | 9/2017 | Morales et al. | |
| 2017/0348055 A1* | 12/2017 | Salcedo | A61C 9/0006 |
| 2019/0239969 A1 | 8/2019 | Abu-Akeel et al. | |
| 2020/0038160 A1 | 2/2020 | Hornung et al. | |
| 2020/0237265 A1 | 7/2020 | Jaisson | |
| 2023/0149123 A1* | 5/2023 | Fittipaldi | A61C 5/007 |
| | | | 433/24 |

FOREIGN PATENT DOCUMENTS

| | | |
|---|---|---|
| CN | 110072487 A | 7/2019 |
| FR | 3 063 427 | 9/2018 |
| JP | 2017-509450 | 4/2017 |
| JP | 2018-110841 | 7/2018 |
| JP | 2019-506929 | 3/2019 |
| WO | WO 2015/103613 | 7/2015 |
| WO | WO 2018/158551 A | 9/2018 |

* cited by examiner

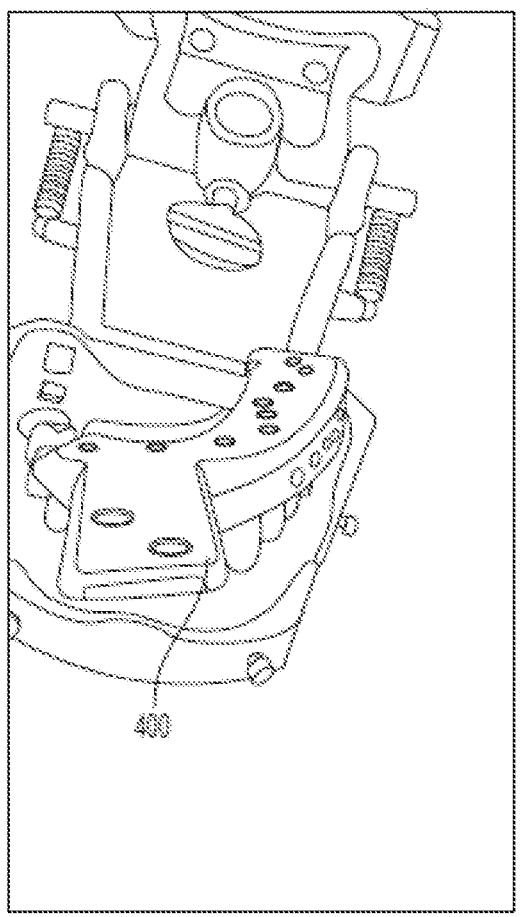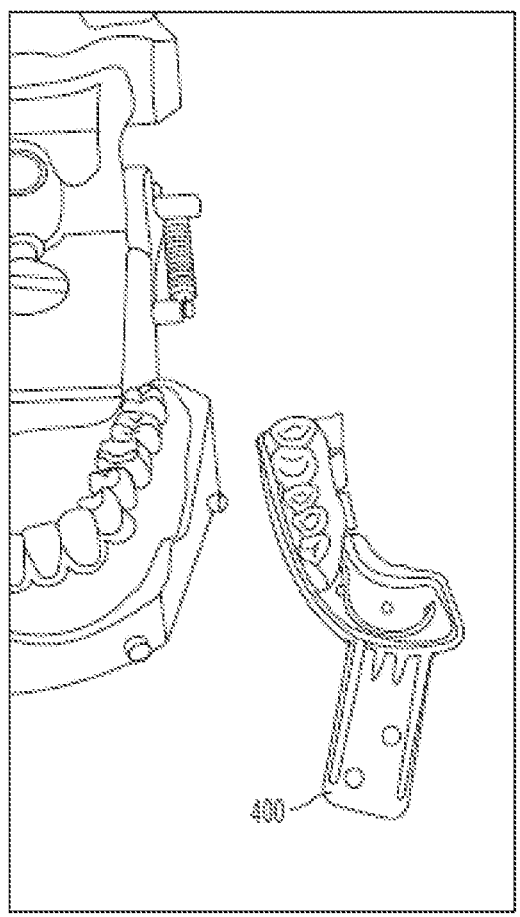
FIG. 2A
PRIOR ART
FIG. 2B
PRIOR ART

SPLINT DEVICE FOR GUIDED SURGICAL ROBOT

CROSS-REFERENCE TO RELATED APPLICATIONS

This application is a national stage filing under 35 U.S.C. 371 of PCT/IB2021/052646, filed Mar. 30, 2021, which International Application was published by the International Bureau in English on Oct. 7, 2021, as WO 2021/198919, and application claims priority from U.S. Provisional Application No. 63/001,998, filed on Mar. 30, 2020, which applications are hereby incorporated in their entirety by reference in this application.

BACKGROUND

Field of the Disclosure

The present application relates to surgical robots and associated guidance systems and, more particularly, to a splint device for forming a fiducial marker and/or a tracking marker for the guidance system of a surgical robot.

Description of Related Art

Robotic systems are being increasingly implemented in surgical applications. One such example involves a surgical robot used in dental surgery. Such robots are often associated with a guidance system used to guide the surgical instrument implemented by the surgical robot. The guidance system may also be configured to be involved in the surgical pre-planning process, whether by being involved in gathering and/or analyzing patient data, and planning the surgical procedure, or by relying upon pre-planning data to guide the surgical instrument to conduct the surgical procedure.

In particular, surgical procedures, some surgical robotic systems rely upon a fixed reference point associated with the patient's body for guiding the surgical robot. That is, some such surgical robotic systems define a frame of reference with respect to the patient's body so as to account or otherwise compensate for movements or motion of the patient during the procedure, whether during pre-planning or during the actual surgical procedure itself. This reference point must also be repeatable such that multiple engagements/disengagements (i.e., periods between pre-planning and the actual surgical procedure) do not change the frame of reference implemented by the surgical robot or the guidance system associated therewith.

In particular instances, the reference point (or the connection between the guidance system and the patient to define that reference point) implemented by the guidance system for the surgical robot may be accomplished through, for example, an optical modality, a mechanical modality, an acoustic modality, or other suitable and appropriate tracking/guiding modality, or combination thereof. In some modalities, particularly used in dental surgery applications, one mechanical modality for forming the reference point (i.e., a "fiducial marker") may be accomplished, for example, by attaching/securing a rigid element to the head/teeth of the patient. Such a rigid element, in some instances, may be referred to as and may comprise a splint (see, e.g., prior art in FIGS. 1, 2A, and 2B). Such a splint may generally include, for instance, a retainer portion that grips one or more of the teeth (i.e., by way of an adhesive substance, such as an acrylic material applied between the retainer portion and the teeth), a mounting portion (i.e., mounting arm) that connects the retainer portion to a separate kinematic mount, and the kinematic mount, itself, which may comprise an attachment point for a tracking portion associated with the guidance system for the surgical robot (i.e., wherein, for instance, reflective markers may be mounted to the attachment point for optical tracking of the fiducial marker, or the attachment point may include a securing site for forming a mechanical connection therewith for mechanical tracking of the fiducial marker, or the attachment point may otherwise be configured to receive an appropriate element associated with any other suitable tracking arrangement for the fiducial marker).

In such instances, it may be preferable for the retainer portion to be as rigid as possible (i.e., the structure of the retainer itself, as well as the fixation thereof to the teeth of the patient) throughout the surgical procedure. However, it may also be preferable for the retainer portion to be readily removable when the surgical procedure is complete. In some instances, it may be preferable for the splint to be reproducibly removed and replaced, for example, between the pre-planning procedure (i.e., a CT scan) which may occur on one day (when the splint must be in place so the fiducial marker(s) associated therewith are captured in the scan), and the surgical procedure may occur on another day (wherein the surgical procedure requires the splint to be in place for tracking/guiding the surgical procedure). In other instances, it may be preferable that a single splint configuration be usable or adaptable across a wide population of patients, for example, as a universal fit device. Further, it may be desirable to have a minimum of separate components of the splint, or if separate components are included, that such separate components are integrated into or are firmly and securely affixed as part of the overall splint assembly.

Prior art splint devices as shown, for example, in FIGS. 1, 2A, and 2B, also require a careful balance of the adhesive material (i.e., dental acrylic) to be applied in order to be effective in rigidly mounting the retainer portion to the teeth of the patient. For instance, if too little of the adhesive material is applied in the retainer portion, the splint device may be too easily separated from the teeth, since the amount of the adhesive material may not be sufficient to bond the retainer portion to the teeth to sufficiently resist the forces applied thereto during the surgical procedure. However, if too much of the adhesive material is applied to the retainer portion, the excess adhesive material may flows into the tooth undercuts (i.e., the portion of the tooth where the tooth narrows toward the gum-line and/or the spaces between teeth), the retainer portion will not be readily removable at the end of the surgical procedure, without, for instance, drilling into the solidified adhesive material to remove the retainer portion from the tooth/teeth. In such instances, the retainer portion will likely not be re-usable for the particular patient, and if further procedures are required, a new retainer portion, including a new mounting portion for the fiducial marker and/or tracking marker, may also be required.

As such, there exists a need for a splint device for forming a fiducial marker for the guidance system of a surgical robot used, for example, in dental surgery which addresses these and other limitations of prior art devices.

SUMMARY OF THE DISCLOSURE

The above and other needs are met by aspects of the present disclosure which, in one particular aspect, provides a splint device for robotically-guided surgery. Such a device comprises an elongate first splint portion having first and second longitudinal ends and defining longitudinally spaced-apart relief holes; and an elongate second splint portion having first and second longitudinal ends and defining longitudinally spaced-apart relief holes, with the second splint portion co-extending with the first splint portion. A first separability provision is disposed between the first and second splint portions, and extends longitudinally from between the respective first ends to between the respective second ends of the first and second splint portions. A tracking portion is engaged with the first splint portion or the second splint portion and extends outwardly therefrom, wherein the tracking portion has a kinematic mount engaged therewith. A second separability provision extends between one of the relief holes of the first splint portion and one of the relief holes of the second splint portion, wherein the second separability provision is arranged to be severable so as to facilitate adjustability of a length of the first and second splint portions and the first separability provision.

Another aspect of the present disclosure provides a splint device for robotically-guided surgery. Such a device comprises an elongate first splint portion having first and second longitudinal ends and defining longitudinally spaced-apart relief holes; and an elongate second splint portion having first and second longitudinal ends and defining longitudinally spaced-apart relief holes, with the second splint portion co-extending with the first splint portion. A first separability provision is disposed between the first and second splint portions and extends longitudinally from between the respective first ends to between the respective second ends of the first and second splint portions. A tracking portion is engaged with the first splint portion or the second splint portion and extends outwardly therefrom, wherein the tracking portion has a kinematic mount engaged therewith. A tool calibration provision is engaged with the first splint portion, the second splint portion, the first separability provision, or the tracking portion, wherein the tool calibration provision is disposed in a predetermined disposition relative to the kinematic mount.

Yet another aspect of the present disclosure provides a splint device for robotically-guided surgery. Such a device comprises an elongate first splint portion having first and second longitudinal ends and defining longitudinally spaced-apart relief holes; and an elongate second splint portion having first and second longitudinal ends and defining longitudinally spaced-apart relief holes, with the second splint portion co-extending with the first splint portion. A first separability provision is disposed between the first and second splint portions and extends longitudinally from between the respective first ends to between the respective second ends of the first and second splint portions. A tracking portion is engaged with the first splint portion or the second splint portion and extends outwardly therefrom, wherein the tracking portion has a kinematic mount engaged therewith. A fiducial marker element is received by a depression defined by an outer surface of the first splint portion, the second splint portion, the first separability provision, or the tracking portion, wherein the fiducial marker element is received in a predetermined disposition relative to the kinematic mount.

The present disclosure thus includes, without limitation, the following example embodiments:

Example Embodiment 1: A splint device for robotically-guided surgery, said device comprising an elongate first splint portion having first and second longitudinal ends and defining longitudinally spaced-apart relief holes; an elongate second splint portion having first and second longitudinal ends and defining longitudinally spaced-apart relief holes, the second splint portion co-extending with the first splint portion; a first separability provision disposed between the first and second splint portions and extending longitudinally from between the respective first ends to between the respective second ends of the first and second splint portions; a tracking portion engaged with the first splint portion or the second splint portion and extending outwardly therefrom, the tracking portion having a kinematic mount engaged therewith; and a second separability provision extending between one of the relief holes of the first splint portion and one of the relief holes of the second splint portion, wherein the second separability provision is arranged to be severable so as to facilitate adjustability of a length of the first and second splint portions and the first separability provision.

Example Embodiment 2: The device of any preceding or subsequent example embodiment, or combinations thereof, wherein the kinematic mount is integrally formed with the tracking portion.

Example Embodiment 3: The device of any preceding or subsequent example embodiment, or combinations thereof, wherein the tracking portion extends from the first or second end of the first or second splint portion.

Example Embodiment 4: The device of any preceding or subsequent example embodiment, or combinations thereof, wherein the second separability provision comprises a reduced section thickness of the first and second splint portions between the one of the relief holes of the first splint portion and the one of the relief holes of the second splint portion.

Example Embodiment 5: The device of any preceding or subsequent example embodiment, or combinations thereof, wherein the first and second splint portions and the first separability provision interact to collectively form an elongate channel having an inner surface defining a concavity, and wherein the first separability provision defines a reduced section thickness between and in relation to the first and second splint portions, so as to define a slot in the inner surface extending between the respective first and second ends of the first and second splint portions.

Example Embodiment 6: The device of any preceding or subsequent example embodiment, or combinations thereof, wherein the slot is arranged to receive a divider, the divider extending along the slot such that the divider and the first splint portion define a first portion of the elongate channel, and the divider and the second splint portion define a second portion of the elongate channel.

Example Embodiment 7: The device of any preceding or subsequent example embodiment, or combinations thereof, wherein the first separability provision defines one or more holes each extending from an outer surface of the elongate channel to the slot, the one or more holes being spaced apart along the first separability provision between the respective first and second ends of the first and second splint portions.

Example Embodiment 8: The device of any preceding or subsequent example embodiment, or combinations thereof, comprising a fiducial marker element received by a depression defined by an outer surface of the first splint portion, the second splint portion, the first separability provision, or the tracking portion, the fiducial marker element being received in a predetermined disposition relative to the kinematic mount.

Example Embodiment 9: The device of any preceding or subsequent example embodiment, or combinations thereof, wherein the fiducial marker element is spherical and the depression is hemispherical or an elongate concave channel arranged to receive the spherical fiducial marker element.

Example Embodiment 10: The device of any preceding or subsequent example embodiment, or combinations thereof, comprising a tool calibration provision engaged with the first splint portion, the second splint portion, the first separability provision, or the tracking portion, the tool calibration provision being disposed in a predetermined disposition relative to the kinematic mount.

Example Embodiment 11: A splint device for robotically-guided surgery, said device comprising an elongate first splint portion having first and second longitudinal ends and defining longitudinally spaced-apart relief holes; an elongate second splint portion having first and second longitudinal ends and defining longitudinally spaced-apart relief holes, the second splint portion co-extending with the first splint portion; a first separability provision disposed between the first and second splint portions and extending longitudinally from between the respective first ends to between the respective second ends of the first and second splint portions; a tracking portion engaged with the first splint portion or the second splint portion and extending outwardly therefrom, the tracking portion having a kinematic mount engaged therewith; and a tool calibration provision engaged with the first splint portion, the second splint portion, the first separability provision, or the tracking portion, the tool calibration provision being disposed in a predetermined disposition relative to the kinematic mount.

Example Embodiment 12: The device of any preceding or subsequent example embodiment, or combinations thereof, wherein the kinematic mount is integrally formed with the tracking portion.

Example Embodiment 13: The device of any preceding or subsequent example embodiment, or combinations thereof, wherein the tracking portion extends from the first or second end of the first or second splint portion.

Example Embodiment 14: The device of any preceding or subsequent example embodiment, or combinations thereof, comprising a fiducial marker element received by a depression defined by an outer surface of the first splint portion, the second splint portion, the first separability provision, or the tracking portion, the fiducial marker element being received in a predetermined disposition relative to the kinematic mount.

Example Embodiment 15: The device of any preceding or subsequent example embodiment, or combinations thereof, wherein the fiducial marker element is spherical and the depression is hemispherical or an elongate concave channel arranged to receive the spherical fiducial marker element.

Example Embodiment 16: The device of any preceding or subsequent example embodiment, or combinations thereof, comprising a second separability provision extending between one of the relief holes of the first splint portion and one of the relief holes of the second splint portion, wherein the second separability provision is arranged to be severable so as to facilitate adjustability of a length of the first and second splint portions and the first separability provision.

Example Embodiment 17: The device of any preceding or subsequent example embodiment, or combinations thereof, wherein the second separability provision comprises a reduced section thickness of the first and second splint portions between the one of the relief holes of the first splint portion and the one of the relief holes of the second splint portion.

Example Embodiment 18: The device of any preceding or subsequent example embodiment, or combinations thereof, wherein the first and second splint portions and the first separability provision interact to collectively form an elongate channel having an inner surface defining a concavity, and wherein the first separability provision defines a reduced section thickness between and in relation to the first and second splint portions, so as to define a slot in the inner surface extending between the respective first and second ends of the first and second splint portions.

Example Embodiment 19: The device of any preceding or subsequent example embodiment, or combinations thereof, wherein the slot is arranged to receive a divider, the divider extending along the slot such that the divider and the first splint portion define a first portion of the elongate channel, and the divider and the second splint portion define a second portion of the elongate channel.

Example Embodiment 20: The device of any preceding or subsequent example embodiment, or combinations thereof, wherein the first separability provision defines one or more holes each extending from an outer surface of the elongate channel to the slot, the one or more holes being spaced apart along the first separability provision between the respective first and second ends of the first and second splint portions.

Example Embodiment 21: A splint device for robotically-guided surgery, said device comprising an elongate first splint portion having first and second longitudinal ends and defining longitudinally spaced-apart relief holes; an elongate second splint portion having first and second longitudinal ends and defining longitudinally spaced-apart relief holes, the second splint portion co-extending with the first splint portion; a first separability provision disposed between the first and second splint portions and extending longitudinally from between the respective first ends to between the respective second ends of the first and second splint portions; a tracking portion engaged with the first splint portion or the second splint portion and extending outwardly therefrom, the tracking portion having a kinematic mount engaged therewith; and a fiducial marker element received by a depression defined by an outer surface of the first splint portion, the second splint portion, the first separability provision, or the tracking portion, the fiducial marker element being received in a predetermined disposition relative to the kinematic mount.

Example Embodiment 22: The device of any preceding or subsequent example embodiment, or combinations thereof, wherein the kinematic mount is integrally formed with the tracking portion.

Example Embodiment 23: The device of any preceding or subsequent example embodiment, or combinations thereof, wherein the tracking portion extends from the first or second end of the first or second splint portion.

Example Embodiment 24: The device of any preceding or subsequent example embodiment, or combinations thereof, wherein the fiducial marker element is spherical and the depression is hemispherical or an elongate concave channel arranged to receive the spherical fiducial marker element.

Example Embodiment 25: The device of any preceding or subsequent example embodiment, or combinations thereof, comprising a second separability provision extending between one of the relief holes of the first splint portion and one of the relief holes of the second splint portion, wherein the second separability provision is arranged to be severable so as to facilitate adjustability of a length of the first and second splint portions and the first separability provision.

Example Embodiment 26: The device of any preceding or subsequent example embodiment, or combinations thereof, wherein the second separability provision comprises a reduced section thickness of the first and second splint portions between the one of the relief holes of the first splint portion and the one of the relief holes of the second splint portion.

Example Embodiment 27: The device of any preceding or subsequent example embodiment, or combinations thereof, wherein the first and second splint portions and the first separability provision interact to collectively form an elongate channel having an inner surface defining a concavity, and wherein the first separability provision defines a reduced section thickness between and in relation to the first and second splint portions, so as to define a slot in the inner surface extending between the respective first and second ends of the first and second splint portions.

Example Embodiment 28: The device of any preceding or subsequent example embodiment, or combinations thereof, wherein the slot is arranged to receive a divider, the divider extending along the slot such that the divider and the first splint portion define a first portion of the elongate channel, and the divider and the second splint portion define a second portion of the elongate channel.

Example Embodiment 29: The device of any preceding or subsequent example embodiment, or combinations thereof, wherein the first separability provision defines one or more holes each extending from an outer surface of the elongate channel to the slot, the one or more holes being spaced apart along the first separability provision between the respective first and second ends of the first and second splint portions.

Example Embodiment 30: The device of any preceding or subsequent example embodiment, or combinations thereof, comprising a tool calibration provision engaged with the first splint portion, the second splint portion, the first separability provision, or the tracking portion, the tool calibration provision being disposed in a predetermined disposition relative to the kinematic mount.

These and other features, aspects, and advantages of the present disclosure will be apparent from a reading of the following detailed description together with the accompanying drawings, which are briefly described below. The present disclosure includes any combination of two, three, four, or more features or elements set forth in this disclosure, regardless of whether such features or elements are expressly combined or otherwise recited in a specific embodiment description herein. This disclosure is intended to be read holistically such that any separable features or elements of the disclosure, in any of its aspects and embodiments, should be viewed as intended, namely to be combinable, unless the context of the disclosure clearly dictates otherwise.

It will be appreciated that the summary herein is provided merely for purposes of summarizing some example aspects so as to provide a basic understanding of the disclosure. As such, it will be appreciated that the above described example aspects are merely examples and should not be construed to narrow the scope or spirit of the disclosure in any way. It will be appreciated that the scope of the disclosure encompasses many potential aspects, some of which will be further described below, in addition to those herein summarized. Further, other aspects and advantages of such aspects disclosed herein will become apparent from the following detailed description taken in conjunction with the accompanying drawings which illustrate, by way of example, the principles of the described aspects.

BRIEF DESCRIPTION OF THE SEVERAL VIEWS OF THE DRAWING(S)

Figure 3A:
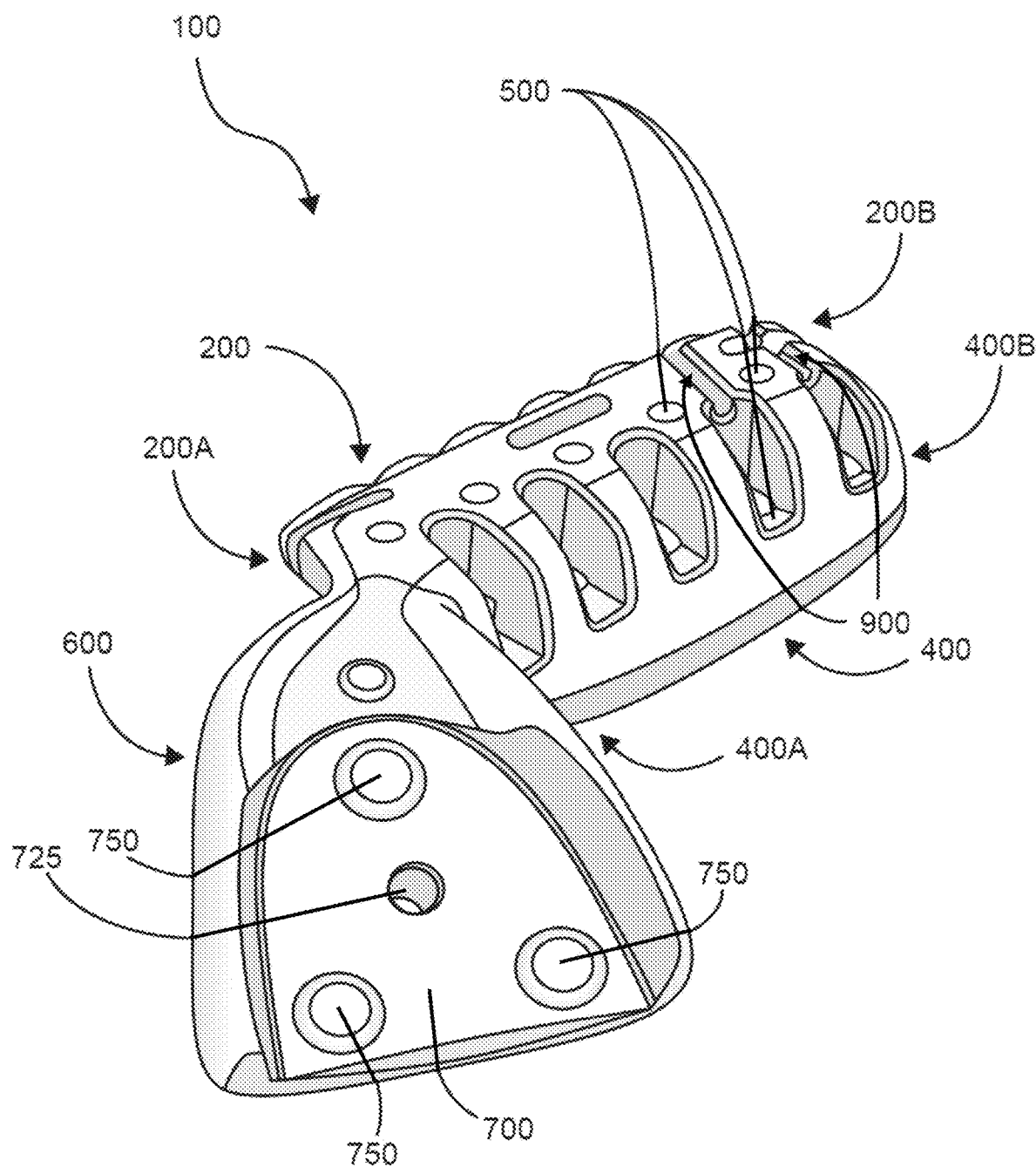
Figure 3B:
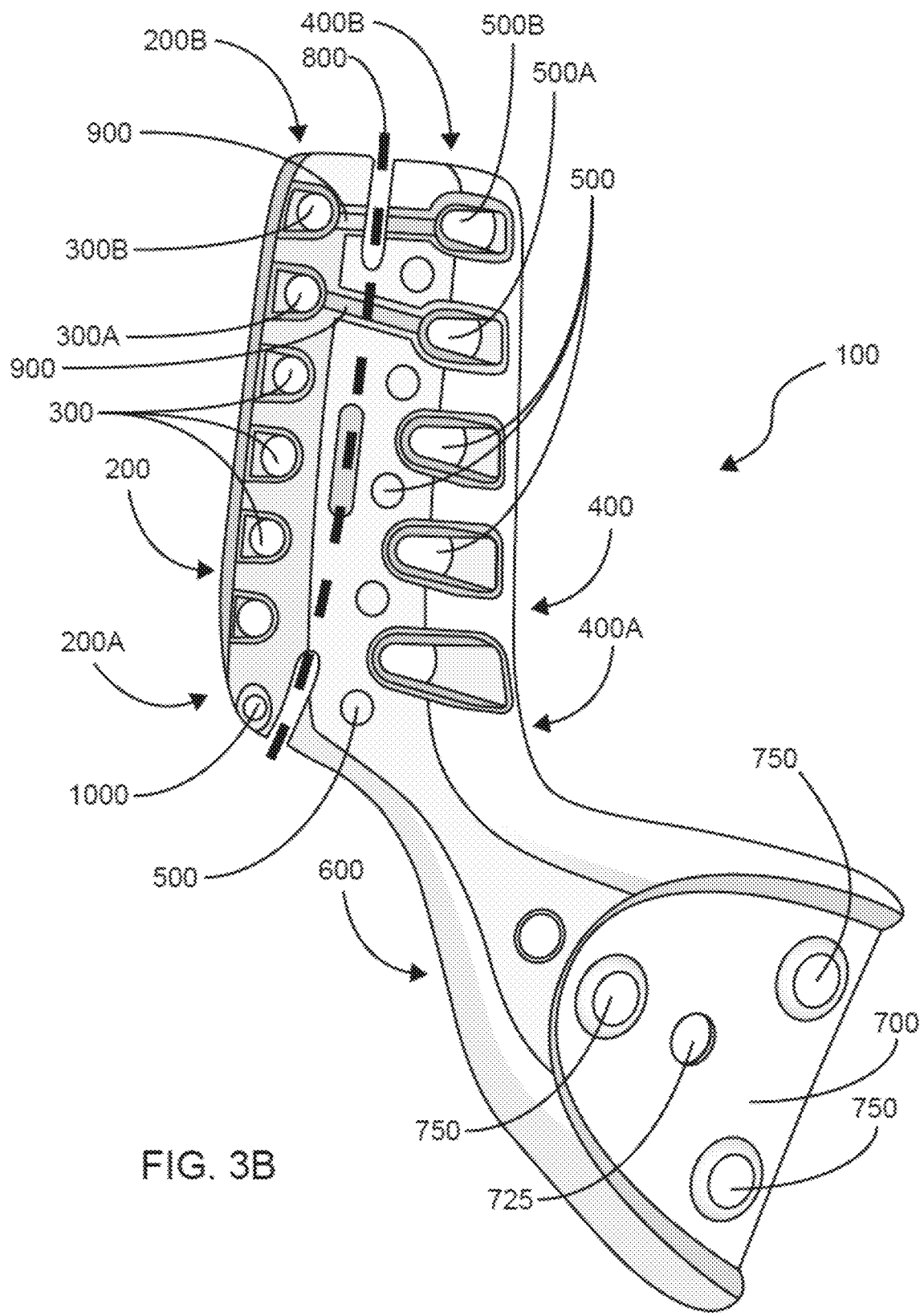
Figure 4A:
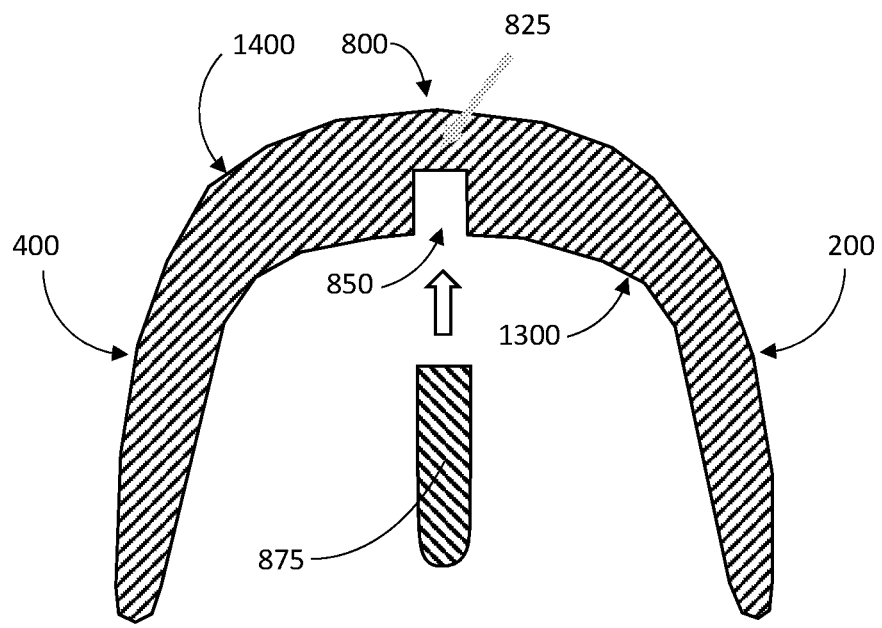
Figure 4B:
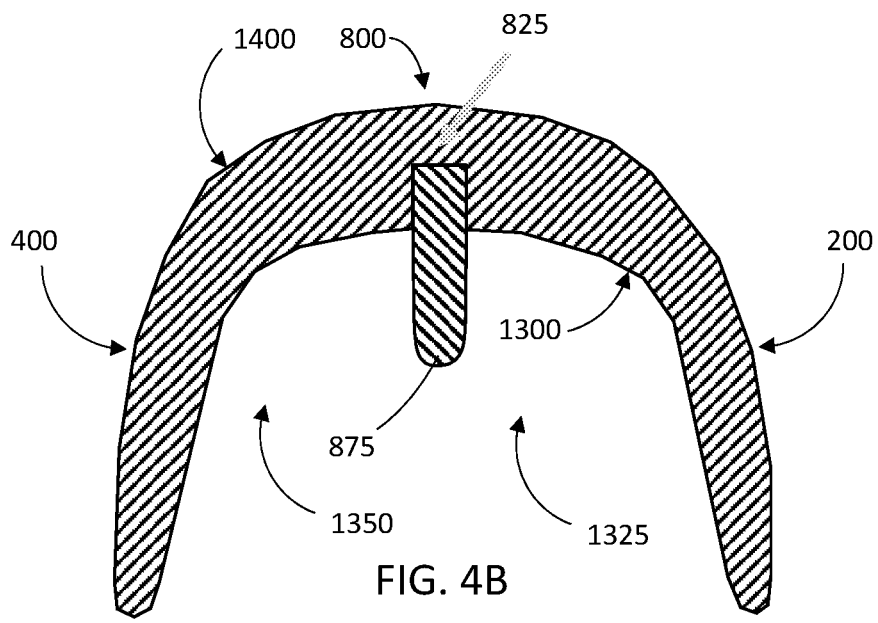
Figure 5A:
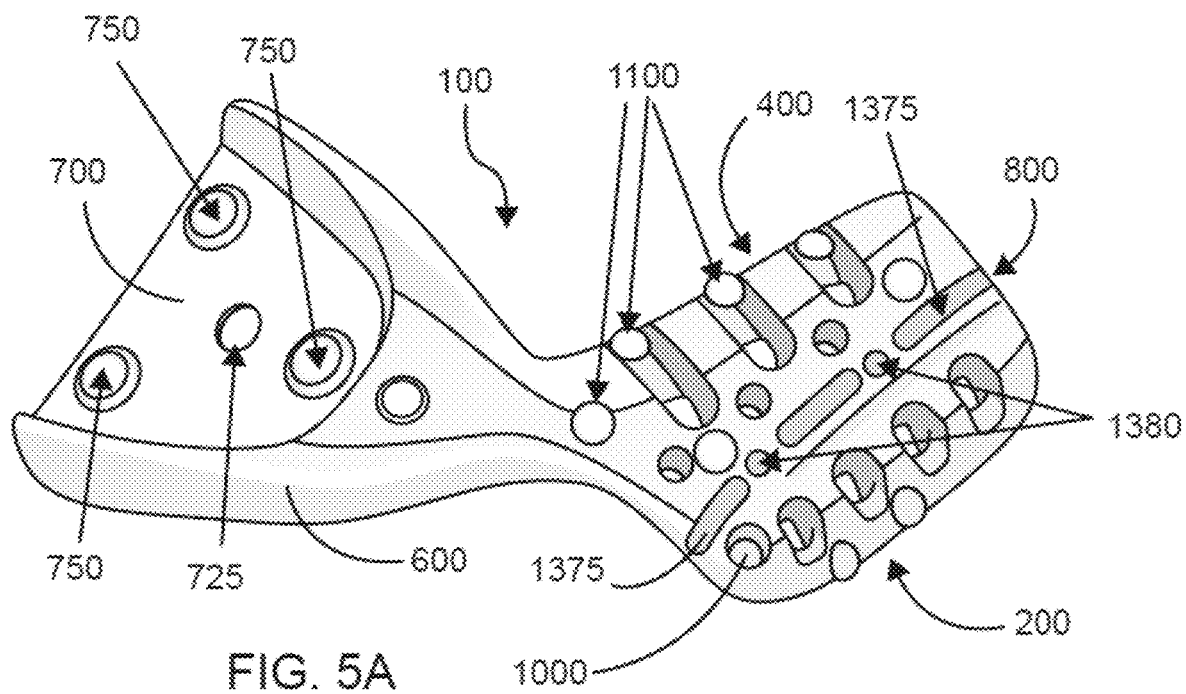
Figure 5B:
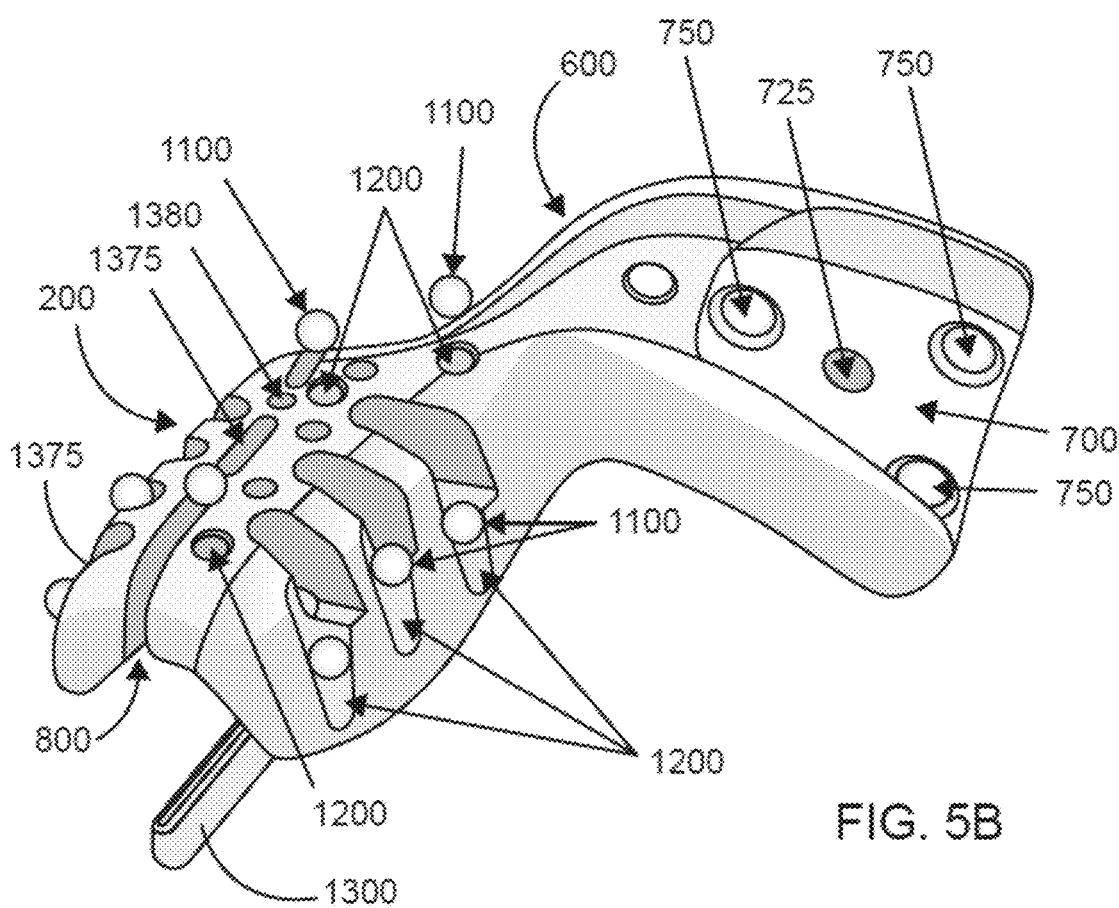

Having thus described the disclosure in general terms, reference will now be made to the accompanying drawings, which are not necessarily drawn to scale, and wherein:

FIG. 1 schematically illustrates a prior art splint device engaged with a representative model of a mouth of a patient so as to provide a fiducial marker and/or a tracking marker for a guidance system for a surgical robot for dental surgeries;

FIGS. 2A and 2B schematically illustrates a prior art splint device engaged with a representative model of a mouth of a patient so as to provide a fiducial marker and/or a tracking marker for a guidance system for a surgical robot for dental surgeries (FIG. 2A) and the prior art splint device disengaged from the representative model of the mouth of the patient (FIG. 2B);

FIGS. 3A and 3B schematically illustrate different perspective views of a splint device arranged to provide a fiducial marker and/or a tracking marker for a guidance system for a surgical robot, according to one aspect of the present disclosure;

FIGS. 4A and 4B schematically illustrate representative cross section elevations of a splint device for a guidance system for a surgical robot, with the splint device configured to facilitate removability, according to one aspect of the present disclosure; and FIGS. 5A and 5B schematically illustrate different perspective views of a splint device providing a fiducial marker arrangement for a guidance system for a surgical robot, according to one aspect of the present disclosure.

DETAILED DESCRIPTION OF THE DISCLOSURE

The present disclosure now will be described more fully hereinafter with reference to the accompanying drawings, in which some, but not all aspects of the disclosure are shown. Indeed, the disclosure may be embodied in many different forms and should not be construed as limited to the aspects set forth herein; rather, these aspects are provided so that this disclosure will satisfy applicable legal requirements. Like numbers refer to like elements throughout.

Particular aspects of the present disclosure, as shown, for example, in FIGS. 3A and 3B provide a splint device 100 for use with a guidance system of a surgical robot, for instance, in dental surgery. One skilled in the art, however, will appreciate that the concept of the splint device disclosed herein as forming a fiducial marker and/or a tracking marker, or otherwise a frame of reference for a surgical robotic system may find applicability to other surgical processes not involving dental surgery, such as, for example, orthopedic surgery, ENT surgery, and neurosurgery. As such, the aspects of the disclosure presented herein are merely examples of the applicability of the disclosed concepts and are not intended to be limiting in any manner.

Such a splint device 100 implemented in conjunction with a guided surgical robot may comprise, for example, an elongate first splint portion 200 having first and second longitudinal ends 200A, 200B and defining longitudinally spaced-apart relief holes 300, and an elongate second splint portion 400 having first and second longitudinal ends 400A, 400B and defining longitudinally spaced-apart relief holes 500, wherein the second splint portion 400 generally coextends with the first splint portion 200. A tracking portion 600 is engaged with the first splint portion 200 or the second splint portion 400, and extends outwardly therefrom. More particularly, in some aspects, the tracking portion 600 extends from the first end 200A, 400A or the second end 200B, 400B of the first or second splint portion 200, 400. In some instances, the tracking portion 600 has a kinematic mount 700 engaged therewith. A first separability provision

800 (see, e.g., FIG. 3B) is disposed between the first and second splint portions 200, 400. In some aspects, the first separability provision 800 extends longitudinally from between the respective first ends 200A, 400A to between the respective second ends 200B, 400B of the first and second splint portions 200, 400.

In some instances, a second separability provision 900 (see, e.g., FIG. 3A) extends between one of the relief holes 300A or 300B of the first splint portion 200 and one of the relief holes 500A or 500B of the second splint portion 400, wherein the second separability provision 900 is arranged to be severable so as to facilitate adjustability of a length of the first and second splint portions 200, 400 and the first separability provision 800. The adjustability of the length of the splint device 100 via the second separability provision 900 can facilitate, for example, the implementation of the splint device 100 to a variety of different size applications (e.g., adult teeth or children's teeth). Moreover, since the splint device 100 is generally applied using an adhesive material (e.g., acrylic), the adherence is a function of surface area adhered with the adhesive material. As such, a shorter splint device will have a lesser adhered surface area than a longer splint device, and will therefore be easier to remove at the end of the procedure than the longer splint device. The second separability provision 900, in some aspects, comprises a reduced section thickness of the first and second splint portions 200, 400 between the one of the relief holes 300 of the first splint portion 200 and the one of the relief holes 500 of the second splint portion 400. The reduced section thickness of the second severability provision 900 can, but does not necessarily, intersect with the slot 850 of the first severability provision 800. In other aspects, multiple second severability provisions 900 can be provided along the first and second splint portions 200, 400 to provide for multiple adjustability of the length of the splint device 100.

In other instances, a tool calibration provision 1000 (see, e.g., FIG. 3B or FIG. 5A) is engaged with the first splint portion 200, the second splint portion 400, the first separability provision 800, or the tracking portion 600, wherein the tool calibration provision 1000 is disposed in a predetermined disposition relative to the kinematic mount 700. The tool calibration provision 1000 may be configured, for example, as a receptacle or other suitable surface feature for receiving the end effector (e.g., a tip of a drill bit) of a surgical instrument affixed to the surgical robot. The tool calibration provision 1000, in some instances, is formed integrally with the particular component of the splint device 100 or, in other instances, can be a separate and discrete element (e.g., a durable element such as a metal element, a ceramic element, or other suitable element). Since the tool calibration provision 1000 is in a known disposition relative to the kinematic mount 700, the tool calibration provision 1000, upon interaction with the end effector of the surgical robot, provides a confirmation or calibration that the end effector is accurately tracked in relation to the surgical robot for conducting a procedure. In some instances, the tool calibration provision 1000 is radiopaque such that the disposition thereof with respect to the kinematic mount 700 can be determined and/or confirmed through imaging analysis.

In yet other instances, a fiducial marker element 1100 (see, e.g., FIGS. 5A and 5B) is received by a depression 1200 defined by an outer surface of the first splint portion 200, the second splint portion 400, the first separability provision 800, or the tracking portion 600, wherein the fiducial marker element 1100 is received in a predetermined disposition relative to the kinematic mount 700. In particular aspects, the splint device 100 defines a plurality of depressions 1200 arranged to receive a plurality of fiducial marker elements 1100. For example, in some aspects, the fiducial marker element 1100 is spherical and the depression 1200 is hemispherical or an elongate concave channel arranged to receive the spherical fiducial marker element 1100. Once secured with the respective depression 1200, whether through an interference fit (e.g., a press fit), by overmolding, or with an adhesive material (e.g., epoxy) disposed with the depression, the fiducial marker element(s) 1100 are essentially embedded within the splint device 100. Moreover, in some aspects, the depressions 1200 are oriented such that the adhesive material (e.g., epoxy) is retained, such as by gravity, at the location in the depression 1200 at which the fiducial marker element 1100 is secured/embedded. Since the fiducial marker element(s) 1100 are radiopaque in some aspects, the fiducial marker element(s) 1100 can be detected through imaging analysis (e.g., a CT scan). Accordingly, in particular instances, the fiducial marker element(s) 1100 are radiopaque and can be differentiated from the splint device 100 (e.g., formed of a plastic/polymeric material) and the adhesive material (e.g., acrylic) used for adhering the splint device 100 to the patient. Since the fiducial marker element(s) 1100 are all embedded with the splint device 100, the field of view of the imaging analysis (e.g., the CT scan) can be reduced.

In some aspects, the first and second splint portions 200, 400 and the first separability provision 800 are integrally formed as a single assembly. In other aspects, the first and second splint portions 200, 400, the first separability provision 800, and the tracking portion 600 are integrally formed as a single assembly. In still other aspects, the kinematic mount 700 is integrally formed with the tracking portion 600. The kinematic mount 700 (see, e.g., FIGS. 3A-3B or FIGS. 5A-5B), in some instances, defines a central locating receptacle 725 surrounded by three or more angularly spaced-apart protrusions 750. Such a kinematic mount 700 is generally configured to receive a complementarily-configured mount (not shown) including or engaged with a tracking provision. The tracking provision can include, for example, a physically connected tracking provision such as a tracking arm connected to the surgical robot. In other instances, the tracking provision can include, for example, a non-physically connected tracking provision such as an optical tracking device, a magnetic tracking device, a wireless or WiFi tracking device, an electromagnetic tracking device, an inductive tracking device, or any other form of tracking device that does not require a physical connection between the tracking provision affixed to the kinematic mount 700 and the surgical robot. In either instance, the integration of the kinematic mount 700 into the tracking portion 600 provides for repeatable engagement with the tracking provision, with interchangeable engagement between different types of tracking provisions. The integration of the kinematic mount 700 can further be accomplished, for example, through molding, machining, and or 3D printing. In yet other aspects, the second separability provision 900, the tool calibration provision 1000, and/or the depression(s) 1200 are integral with the overall assembly of the splint device 100. When formed as an integral assembly, the splint device 100 may be formed, for example, using any suitable formation procedure such as injection molding, casting, or machining, as necessary or appropriate.

In some aspects, the first and second splint portions 200, 400 and the first separability provision 800 interact to collectively form an elongate channel (see, e.g., FIGS. 4A-4B) having an inner surface 1300 defining a concavity (e.g., a "U" channel), and wherein the first separability provision 800 defines a reduced section thickness 825 between and in relation to the first and second splint portions 200, 400. The first and second splint portions 200, 400 cooperate with the reduced section thickness 825 to define a slot 850 in the inner surface 1300, wherein the slot 850 extends longitudinally between the respective first ends 200A, 400A and second ends 200B, 400B of the first and second splint portions 200, 400. The slot 850 is arranged to receive a divider 875, wherein the divider 875 extends along the slot 850. Accordingly, the divider 875 and the first splint portion 200 cooperate to define a first longitudinally-extending portion 1325 of the elongate channel, and the divider 875 and the second splint portion 400 cooperate to define a second longitudinally-extending portion 1350 of the elongate channel. In such instances, the longitudinally co-extending first and second portions 1325, 1350 of the elongate channel are separated by the divider 875 such that, for example, an adhesive material deposited in the first portion 1325 will not interact with or contact an adhesive material deposited in the second portion 1350.

Any excess adhesive material within the first and/or second portions 1325, 1350 of the elongate channel are otherwise relieved by flow of the adhesive material out of the elongate channel through the respective relief holes 300, 500 toward the outer surface 1400. In this manner, upon removal of the splint device 100, the first separability provision 800 can be severed as appropriate (e.g., by a drill, a saw, a cutter, or any other suitable severing device) along the entire length thereof (e.g., from the first ends 200A, 400 A to the second ends 200B, 400B) of the first and second splint portions 200, 400. In some aspects, the divider 875 (see, e.g., FIG. 5B) can be a different material, different color, etc. from the first and second splint portions 200, 400 and the first separability provision 800 so as to provide an indicium of appropriate severing of the first separability provision 800 (i.e., the divider 875 will appear as a different color, different material, etc. when the first separability provision 800 is completely severed so as to allow the splint device 100 to be removed). In addition, since the divider 875 (see, e.g., FIG. 4B) extends into the elongate channel (i.e., effectively separating the first separability provision 800 from the underlying teeth to which the splint device 100 is applied), the divider 875 may also protect the underlying teeth from damage from the tool used to sever the first separability provision 800 by providing the indicium of suitable severing of the first separability provision 800 before reaching the underlying teeth. Upon the first separability provision 800 being suitably severed, the first and second splint portions 200, 400 are then separately removed by applying a removal force in opposite directions to each of the first and second splint portions 200, 400, since there is no or limited interaction between adhesive materials deposited in the first and second portions 1325, 1350 of the elongate channel.

In some aspects, the first separability provision 800 (see, e.g., FIGS. 3A-3B or FIGS. 5A-5B) defines one or more holes and/or slots 1375 each extending from an outer surface 1400 of the elongate channel through the reduced section thickness 825 and to the slot 850, wherein the one or more holes and/or slots 1375 are spaced apart (longitudinally) along the first separability provision 800 between the respective first ends 200A, 400A and second ends 200B, 400B of the first and second splint portions 200, 400. In some aspects, the holes/slots 1375 can be supplemented, for example, by one or more depressions or concavities 1380 interspersed between successive holes/slots 1375, wherein the depressions/concavities 1380 can cooperate with the holes/slots 1375 to serve as guides for a cutting/severing tool. Accordingly, severing the first separability provision 800, such as by cutting through the reduced section thickness 825 to reach the slot 850/divider 875, thus allows the splint device 100 to be removed in separate sections such as by applying forces in opposite directions to the first and second splint portions 200, 400.

Many modifications and other embodiments of the inventions set forth herein will come to mind to one skilled in the art to which these disclosed embodiments pertain having the benefit of the teachings presented in the foregoing descriptions and the associated drawings. Therefore, it is to be understood that embodiments of the invention are not to be limited to the specific embodiments disclosed and that modifications and other embodiments are intended to be included within the scope of the invention. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the disclosure. In this regard, for example, different combinations of elements and/or functions than those explicitly described above are also contemplated within the scope of the disclosure. Although specific terms are employed herein, they are used in a generic and descriptive sense only and not for purposes of limitation.

It should be understood that although the terms first, second, etc. may be used herein to describe various steps or calculations, these steps or calculations should not be limited by these terms. These terms are only used to distinguish one operation or calculation from another. For example, a first calculation may be termed a second calculation, and, similarly, a second step may be termed a first step, without departing from the scope of this disclosure. As used herein, the term "and/or" and the "/" symbol includes any and all combinations of one or more of the associated listed items.

As used herein, the singular forms "a", "an" and "the" are intended to include the plural forms as well, unless the context clearly indicates otherwise. It will be further understood that the terms "comprises", "comprising", "includes", and/or "including", when used herein, specify the presence of stated features, integers, steps, operations, elements, and/or components, but do not preclude the presence or addition of one or more other features, integers, steps, operations, elements, components, and/or groups thereof. Therefore, the terminology used herein is for the purpose of describing particular embodiments only and is not intended to be limiting.

That which is claimed:

1. A splint device for robotically-guided surgery, said device comprising:
   an elongate first splint portion having first and second longitudinal ends and defining longitudinally spaced-apart relief holes;
   an elongate second splint portion having first and second longitudinal ends and defining longitudinally spaced-apart relief holes, the second splint portion co-extending with the first splint portion;
   a first separability provision disposed between the first and second splint portions and extending longitudinally from between the respective first ends to between the respective second ends of the first and second splint portions;
   a tracking portion engaged with the first splint portion or the second splint portion and extending outwardly therefrom, the tracking portion having a kinematic mount engaged therewith; and a second separability provision extending between one of the relief holes of the first splint portion and one of the relief holes of the second splint portion, the second separability provision comprising a reduced section thickness of the first and second splint portions extending between the one of the relief holes of the first splint portion and the one of the relief holes of the second splint portion, wherein the second separability provision is arranged to be severable so as to facilitate adjustability of a length of the first and second splint portions and the first separability provision.

2. The device of claim 1, wherein the kinematic mount is integrally formed with the tracking portion.

3. The device of claim 1, wherein the tracking portion extends from the first or second end of the first or second splint portion.

4. The device of claim 1, wherein the first and second splint portions and the first separability provision interact to collectively form an elongate channel having an inner surface defining a concavity, and wherein the first separability provision defines a reduced section thickness between and in relation to the first and second splint portions, so as to define a slot in the inner surface extending between the respective first and second ends of the first and second splint portions.

5. The device of claim 4, wherein the slot is arranged to receive a divider, the divider extending along the slot such that the divider and the first splint portion define a first portion of the elongate channel, and the divider and the second splint portion define a second portion of the elongate channel.

6. The device of claim 4, wherein the first separability provision defines one or more holes each extending from an outer surface of the elongate channel to the slot, the one or more holes being spaced apart along the first separability provision between the respective first and second ends of the first and second splint portions.

7. The device of claim 1, comprising a fiducial marker element received by a depression defined by an outer surface of the first splint portion, the second splint portion, the first separability provision, or the tracking portion, the fiducial marker element being received in a predetermined disposition relative to the kinematic mount.

8. The device of claim 7, wherein the fiducial marker element is spherical and the depression is hemispherical or an elongate concave channel arranged to receive the spherical fiducial marker element.

9. The device of claim 1, comprising a tool calibration provision engaged with the first splint portion, the second splint portion, the first separability provision, or the tracking portion, the tool calibration provision being disposed in a predetermined disposition relative to the kinematic mount.

10. A splint device for robotically-guided surgery, said device comprising:
an elongate first splint portion having first and second longitudinal ends and defining longitudinally spaced-apart relief holes;
an elongate second splint portion having first and second longitudinal ends and defining longitudinally spaced-apart relief holes, the second splint portion co-extending with the first splint portion;
a first separability provision disposed between the first and second splint portions and extending longitudinally from between the respective first ends to between the respective second ends of the first and second splint portions;

a tracking portion engaged with the first splint portion or the second splint portion and extending outwardly therefrom, the tracking portion having a kinematic mount engaged therewith;

a second separability provision extending between one of the relief holes of the first splint portion and one of the relief holes of the second splint portion, the second separability provision comprising a reduced section thickness of the first and second splint portions extending between the one of the relief holes of the first splint portion and the one of the relief holes of the second splint portion, wherein the second separability provision is arranged to be severable so as to facilitate adjustability of a length of the first and second splint portions and the first separability provision; and a tool calibration provision engaged with the first splint portion, the second splint portion, the first separability provision, or the tracking portion, the tool calibration provision being disposed in a predetermined disposition relative to the kinematic mount.

11. The device of claim 10, wherein the kinematic mount is integrally formed with the tracking portion.

12. The device of claim 10, wherein the tracking portion extends from the first or second end of the first or second splint portion.

13. The device of claim 10, comprising a fiducial marker element received by a depression defined by an outer surface of the first splint portion, the second splint portion, the first separability provision, or the tracking portion, the fiducial marker element being received in a predetermined disposition relative to the kinematic mount.

14. The device of claim 13, wherein the fiducial marker element is spherical and the depression is hemispherical or an elongate concave channel arranged to receive the spherical fiducial marker element.

15. The device of claim 10, wherein the first and second splint portions and the first separability provision interact to collectively form an elongate channel having an inner surface defining a concavity, and wherein the first separability provision defines a reduced section thickness between and in relation to the first and second splint portions, so as to define a slot in the inner surface extending between the respective first and second ends of the first and second splint portions.

16. The device of claim 15, wherein the slot is arranged to receive a divider, the divider extending along the slot such that the divider and the first splint portion define a first portion of the elongate channel, and the divider and the second splint portion define a second portion of the elongate channel.

17. The device of claim 15, wherein the first separability provision defines one or more holes each extending from an outer surface of the elongate channel to the slot, the one or more holes being spaced apart along the first separability provision between the respective first and second ends of the first and second splint portions.

18. A splint device for robotically-guided surgery, said device comprising:
an elongate first splint portion having first and second longitudinal ends and defining longitudinally spaced-apart relief holes;
an elongate second splint portion having first and second longitudinal ends and defining longitudinally spaced-apart relief holes, the second splint portion co-extending with the first splint portion;
a first separability provision disposed between the first and second splint portions and extending longitudinally from between the respective first ends to between the respective second ends of the first and second splint portions;

a tracking portion engaged with the first splint portion or the second splint portion and extending outwardly therefrom, the tracking portion having a kinematic mount engaged therewith;

a second separability provision extending between one of the relief holes of the first splint portion and one of the relief holes of the second splint portion, the second separability provision comprising a reduced section thickness of the first and second splint portions extending between the one of the relief holes of the first splint portion and the one of the relief holes of the second splint portion, wherein the second separability provision is arranged to be severable so as to facilitate adjustability of a length of the first and second splint portions and the first separability provision; and a fiducial marker element received by a depression defined by an outer surface of the first splint portion, the second splint portion, the first separability provision, or the tracking portion, the fiducial marker element being received in a predetermined disposition relative to the kinematic mount.

19. The device of claim 18, wherein the kinematic mount is integrally formed with the tracking portion.

20. The device of claim 18, wherein the tracking portion extends from the first or second end of the first or second splint portion.

21. The device of claim 18, wherein the fiducial marker element is spherical and the depression is hemispherical or an elongate concave channel arranged to receive the spherical fiducial marker element.

22. The device of claim 18, wherein the first and second splint portions and the first separability provision interact to collectively form an elongate channel having an inner surface defining a concavity, and wherein the first separability provision defines a reduced section thickness between and in relation to the first and second splint portions, so as to define a slot in the inner surface extending between the respective first and second ends of the first and second splint portions.

23. The device of claim 22, wherein the slot is arranged to receive a divider, the divider extending along the slot such that the divider and the first splint portion define a first portion of the elongate channel, and the divider and the second splint portion define a second portion of the elongate channel.

24. The device of claim 22, wherein the first separability provision defines one or more holes each extending from an outer surface of the elongate channel to the slot, the one or more holes being spaced apart along the first separability provision between the respective first and second ends of the first and second splint portions.

25. The device of claim 18, comprising a tool calibration provision engaged with the first splint portion, the second splint portion, the first separability provision, or the tracking portion, the tool calibration provision being disposed in a predetermined disposition relative to the kinematic mount.

* * * * *